United States Patent [19]
Coultas

[11] Patent Number: 5,714,435
[45] Date of Patent: Feb. 3, 1998

[54] COMPOSITIONS COMPRISING FATTY ACIDS COMBINED WITH FLUMETRALIN OR MALEIC HYDRAZIDE

[75] Inventor: Jeff Coultas, Raleigh, N.C.

[73] Assignee: Mycogen Corporation, San Diego, Calif.

[21] Appl. No.: 668,306

[22] Filed: Jun. 25, 1996

Related U.S. Application Data

[62] Division of Ser. No. 483,596, Jun. 7, 1995, Pat. No. 5,541,153, which is a continuation of Ser. No. 226,097, Apr. 11, 1994, abandoned, which is a continuation of Ser. No. 913,574, Jul. 14, 1992, abandoned.

[51] Int. Cl.$^6$ .................. A01N 43/58; A01N 37/02; A01N 33/18
[52] U.S. Cl. .................. 504/137; 504/185; 504/186
[58] Field of Search .................. 504/185, 186, 504/137

[56] References Cited

U.S. PATENT DOCUMENTS

| | | |
|---|---|---|
| 3,340,040 | 9/1967 | Tso . |
| 3,989,502 | 11/1976 | Nishiyama et al. ............ 71/78 |
| 4,077,796 | 3/1978 | Kish . |

FOREIGN PATENT DOCUMENTS

| | | |
|---|---|---|
| 968175 | 5/1975 | Canada . |
| 968176 | 5/1975 | Canada . |

OTHER PUBLICATIONS

Tso, T.C. et al. (1965) "Inhibition of Tobacco Auxillary Bud Growth with Fatty Acid Methyl Esters" J. Agr. Food Chem. 13(1):78–81.

Sill, L.Z. et al. (1970) "Relationship Between Azalea Bud Morphology and Effectiveness of Methyl Decanoate, A Chemical Pinching Agent" J. Amer. Hort. Sci. 95(3):270–273.

Nelson, P.V. et al. (1971) "Selective mechanism for the differential destruction of plant tissues by methyl decanoate emulsion" Amer. J. Bot. (58(3):249–254.

Chemical Abstracts (1980) 93:213, abstract No. 2106h.

Chemical Abstracts (1977) 87:201, abstract No. 128687t.

Tso, T. C. "Plant Growth Inhibition by some Fatty Acids and their Analogues" Nature 202:511–512. 1964.

Takematsu et al. "Inhibition of growth of tobacco flower buds" Chem Abs 81:34562x. Abstract of JP 73–098–019. 1973.

The Agrochemicals Handbook, "Flumetralin", Maleic hydrazide. 1987.

Primary Examiner—S. Mark Clardy
Attorney, Agent, or Firm—Saliwanchik, Lloyd & Saliwanchik

[57] ABSTRACT

The subject invention concerns the use of fatty acids in combination with maleic hydrazide to achieve excellent control of tobacco suckers on topped plants. The control of suckers is achieved at low rates of maleic hydrazide, thereby reducing maleic hydrazide residues on harvested tobacco.

8 Claims, No Drawings

COMPOSITIONS COMPRISING FATTY ACIDS COMBINED WITH FLUMETRALIN OR MALEIC HYDRAZIDE

This is a division of application Ser. No. 08/483,596, filed Jun. 7, 1995, now U.S. Pat. No. 5,541,153, which is a continuation of Ser. No. 08/226,097, filed Apr. 11, 1994, abandoned, which is a continuation of Ser. No. 07/913,574, filed Jul. 14, 1992, abandoned.

BACKGROUND OF THE INVENTION

To achieve optimal production from a tobacco crop, growers commonly decapitate ("top") their plants in order to obtain leaves with desired physical properties and chemical composition. The topping process involves removing the stem apex, including flowers and some top leaves, near the stage of plant maturity to stimulate the development of the remaining leaves. Current practice frequently involves topping tobacco plants in the "button" stage, soon after the floral part of the plant begins to appear. As a result of the topping process, tobacco plants produce axillary buds, or "suckers," which must be controlled in order to produce the most desirable tobacco plant. These suckers have to be continuously removed to achieve the purpose of topping. When tobacco plants are not topped for about three weeks after reaching the button stage, yields can be reduced by about 20–25 lbs/acre—about 1%.

In the past, the removal of suckers has been carried out by hand, which is a laborious and time-consuming process. Certain chemical growth-agents have been suggested and are now used by many tobacco growers to achieve economical control of suckers. While some of these chemicals provide adequate inhibition of sucker development and are in commercial use, some chemicals cause a variety of metabolic changes in the tobacco plant and result in leaves of undesirable quality. In addition, there has been some question of undesirable residues of chemical agents in the leaf tissue.

One chemical compound which is extensively used for sucker control in tobacco plants is maleic hydrazide. The use of this compound is particularly common with flue-cured tobacco. Flue-curing is a procedure which is widely used by tobacco growers in the United States wherein heat is applied to the tobacco leaves as a part of the curing process. Fatty alcohols are also extensively used in sucker control programs. As described below, contact agents such as the fatty alcohols are used in an initial stage of sucker control, followed by treatment with a systemic agent such as maleic hydrazide.

Typical procedures for reducing or preventing sucker growth in topped tobacco plants include about 2 to 3 initial treatments with contact agents followed by application of a systemic compound such as maleic hydrazide. As this name implies, contact agents reduce sucker growth by inhibiting the suckers with which these agents come into contact. This direct action on the vegetation is in contrast to systemic products, such as maleic hydrazide, which work by altering the physiology of the plant in such a way so as to inhibit axillary growth. In current practice, fatty alcohols are commonly used as contact agents. Contact alcohol chemicals desiccate tender sucker tissue, while the systemic chemicals retard sucker growth by inhibiting cell division. The use of a contact alcohol allows for earlier topping, which increases yields. Therefore, its purpose is to provide sucker control during the period between early topping and the time the upper leaves are large enough to be sprayed with a systemic chemical without causing injury.

One product which is now commonly used in sucker control programs is flumetralin (Prime+™). This product works through a mechanism involving cellular inhibition but must actually contact the sucker tissue to be effective. Therefore, flumetralin is not truly a systemic agent. Flumetralin can be applied individually or in a tankmix with maleic hydrazide.

Recently, there has been increased concern over residue levels of maleic hydrazide which remain in tobacco after the crop is harvested. Despite this concern, residue levels of maleic hydrazide for flue-cured tobacco showed no significant improvement from 1990 to 1991. One study found that the average maleic hydrazide residue in 1990 was 147 ppm, and in 1991 the average was 140 ppm. European countries are particularly sensitive to the maleic hydrazide problem. In Germany, for example, the recommended standard level is 80 ppm maleic hydrazide in the finished product, while in Italy and Spain, the maximum permissible level is 80 ppm. When the maleic hydrazide in the raw tobacco exceeds the level permitted in the finished product, the cigarette manufacturer must blend the high-maleic hydrazide tobacco with other tobacco with less or no maleic hydrazide. The obvious result is a decreased demand for tobacco with high maleic hydrazide residues. It is expected that the European unification process will ultimately result in 80 ppm maximum applying to all European countries. Since almost 50% of the flue-cured tobacco exported to the United States goes to Europe, the potential adverse economic impact of excessive maleic hydrazide residues is quite significant.

A variety of compounds have been used over the years in attempts to inhibit axillary bud growth. For example, esters of fatty acids have been reported to inhibit axillary bud growth in tobacco (Tso, T. C. [1965] *J. Agr. Food Chem.* 13(1):78–81; Tso, T. C., Canadian Patent No. 968175 issued May 27, 1987; and Tso, T. C., Canadian Patent No. 968176 issued May 27, 1975). Methyl esters of fatty acids have also been reported to be useful as chemical pinching agents (Sill, L. Z., P. V. Nelson [1970] *J. Amer. Hort. Sci.* 995(3):270–273; Nelson, P. V., R. K. Reid [1971] *Amer. J. Bot.* 58(3):249–254). Fatty acids themselves, however, have long been regarded as being too phytotoxic to be useful as chemical pinching agents or axillary bud inhibitors (Tso, T. C. [1964] *Nature* 202(4931):511–512).

There is a great need for new methods of tobacco sucker control which achieve the desired level of control but reduce the amount of potentially dangerous chemical residues left on the tobacco leaves.

BRIEF SUMMARY OF THE INVENTION

The subject invention concerns the discovery that certain fatty acids and fatty acid salts can be used effectively in tobacco sucker management programs. As described more fully herein, fatty acids or their salts can be used as initial contact agents followed by treatment with maleic hydrazide. The fatty acids and salts used herein can also be used in conjunction with maleic hydrazide to achieve effective sucker control at reduced rates of maleic hydrazide. We have discovered that application to tobacco plants of a combination of maleic hydrazide and one or more substituted (or unsubstituted) saturated (or unsaturated) fatty acids (or their salts) results in the effective control of sucker growth. A further aspect of the subject invention concerns the use of flumetralin in conjunction with a fatty acid.

The fatty acids of the subject invention can be from about C7 to about C24 and can be, for example, in the epoxide, cyclopropane, methylated, or hydroxylated forms. The fatty acids of the subject invention can be represented by the following formula:

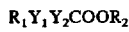

wherein $R_1$=C6 to C23 saturated or unsaturated hydrocarbon, or an epoxide, or cyclopropane thereof $Y_1$=H, C1–C5 hydrocarbon, or hydroxyl at any position along $R_1$ $Y_2$=H, C1–C5 hydrocarbon, or hydroxyl at any position along $R_1$ $R_2$=H, or salt.

Specifically exemplified herein is the use of saturated or unsaturated fatty acids, or their salts, of length C7 to C11 and C17 to C19 in combination with maleic hydrazide. The application of the fatty acids and maleic hydrazide may either be simultaneous or sequential. The use of the compositions described here, when used in the proportions and application rates set forth more fully hereinafter, results in effective sucker control using greatly reduced rates of maleic hydrazide.

The fatty acids or their salts may also be used in one or more of the initial contact treatments which frequently precede application of maleic hydrazide. The C7 to C11 fatty acids are particularly preferred for such use as a contact agent.

One aspect of the subject invention is the provision of novel compositions comprising a mixture of at least one fatty acid or fatty acid salt with maleic hydrazide. The compositions of the present invention comprise a mixture of components wherein said mixture is sufficiently active so that application of the composition enables utilization of reduced amounts of maleic hydrazide while still providing effective sucker control.

Since the level of sucker control obtained following application of the prescribed mixture is generally much superior to that obtained following application of either component alone, the practice of the present invention provides a desirable economic advantage to the user. Furthermore, the reduction in the amount of chemicals introduced into the environment and onto the tobacco leaves is an additional advantageous element of the subject invention.

DETAILED DESCRIPTION OF THE INVENTION

The subject invention pertains to the discovery that certain fatty acids and their salts can be used effectively in programs to control sucker growth on topped tobacco plants. The use of the methods and compositions described herein enables tobacco growers to produce high quality tobacco leaves while substantially reducing the amount of chemicals introduced into the environment and left as residues on the tobacco leaves.

The fatty acids used according to the subject invention can be unsubstituted, or substituted, saturated, or unsaturated, fatty acids (or their salts), of about C7 to about C24. Specifically exemplified are fatty acids of length C7 to C11 and C17 to C19, as typified by, but not limited to, decanoic acid, nonanoic acid, oleic acid, linoleic acid, or linolenic acid. The fatty acid component of the subject invention may be a single fatty acid or a mixture of two or more fatty acids. For brevity, throughout the invention we refer to "fatty acids" and intend this term to cover not only the acids but also various salts of these acids including, but not limited to, sodium, potassium, lithium, magnesium, and amine salts. These salts can be produced using standard procedures well known to those skilled in the art.

Specifically exemplified herein is the use of fatty acids in sucker control programs which further utilize maleic hydrazide. As described above, such programs frequently involve at least 2 to 3 treatments of topped tobacco with a contact agent followed by treatment with maleic hydrazide to achieve effective sucker control until harvest. According to the subject invention, a fatty acid or mixture of fatty acids can be used in the initial contact treatment. The fatty acid can also be used in conjunction with maleic hydrazide, either sequentially or simultaneously, in that phase of the sucker control program. The fatty acid may also be used in conjunction with flumetralin.

Compositions and methods for maleic hydrazide applications are well known to those skilled in the art. For example, a standard recommended rate for maleic hydrazide application is 2.25 lbs/acre, and the chemical is often applied at significantly higher rates such as 3.3 lbs/acre or more. Utilizing the methods of the subject invention, the rate of maleic hydrazide application can be substantially reduced by use in conjunction with at least one fatty acid. The fatty acid may be applied initially followed by a sequential application of maleic hydrazide, or vice versa. Alternatively, the fatty acid and maleic hydrazide may be applied simultaneously.

One embodiment of the present invention consists of the application of a tankmix of a fatty acid and maleic hydrazide. A further embodiment contemplates sequential application of a fatty acid and maleic hydrazide. The sequential applications are contemplated to occur in relatively close temporal proximity such that the plants are subjected to the combined effects of the fatty acid and the maleic hydrazide. In yet another embodiment, the fatty acid is applied one or more times as an initial contact agent, which treatment is followed days or weeks later by treatment with maleic hydrazide or a combined treatment of maleic hydrazide and at least one fatty acid.

Use of a fatty acid with flumetralin (and similar compounds such as butralin and pendimethalin) would be in a manner and at rates analogous to those described herein for use of fatty acids with maleic hydrazide. A person skilled in this art, utilizing the teachings provided herein, would be able to apply fatty acids and flumetralin sequentially or simultaneously to achieve the desired sucker control.

The process of the subject invention is illustrated in the examples which follow. These examples demonstrate the enhanced effects achieved through the use of maleic hydrazide in combination with C9 or C18 fatty acids or their salts.

Following are examples which illustrate procedures, including the best mode, for practicing the invention. These examples should not be construed as limiting. All percentages are by weight and all solvent mixture proportions are by volume unless otherwise noted.

EXAMPLE 1

Control of Tobacco Suckers Using C9 Fatty Acid and Maleic Hydrazide

Seeds of tobacco variety NC37NF were germinated in a greenhouse and later transplanted into 6-inch clay pots using a 1-1-1 ratio of soil, sand, and peat moss. All plants were topped when they reached the 10 to 12 leaf stage. Pelargonic acid (C9) was formulated for application as a 60% a.i. emulsifiable concentrate in 30% Sun Oil 11N and 10% emulsifiers (8% non-ionic and 2% anionic).

Treatments were applied as follows: All treatments were applied in 20 ml total spray volume per plant using a single, hand-held boom equipped with a solid-cone TG-3 tip at 35 psi. All treatments containing more than one chemical or formulation were applied as tank-mix combinations. Individual treatments were applied at the indicated rates. Each treatment consisted of 4 replications with each replication consisting of 1 plant. Evaluations were made by counting and weighing all suckers at about 6 weeks following initial treatment application. The results of these tests are shown below in Table 1. These results show excellent control of suckers using low rates of maleic hydrazide in combination with the C9 fatty acids.

TABLE 1.

Percent control of tobacco suckers achieved using combinations of C9 fatty acids with maleic hydrazide.

| C9 Fatty Acid | Maleic Hydrazide (lb a.i./A) | | |
|---|---|---|---|
| (quarts/acre) | 0 | 0.562 | 1.25 |
| 0 | 0 | 63.3 | 91.8 |
| 0.25 | NT | 54.8 | NT |
| 0.50 | NT | 80.3 | NT |
| 1.0 | 41.8 | 86.6 | NT |
| 2.0 | NT | 91.5 | NT |

NT = not tested

EXAMPLE 2

Control of Tobacco Suckers Using C18 Fatty Acid with Maleic Hydrazide

Seeds of tobacco variety NC37NF were germinated in a greenhouse and later transplanted into 6-inch clay pots using a 1-1-1 ratio of soil, sand, and peat moss. All plants were topped when they reached the 10 to 12 leaf stage. C18 fatty acids were a mixture of oleic, linoleic, and linolenic present at 72%, 20%, and 8%, respectively, in a 60% a.i. formulation with the other ingredients as described for pelargonic acid.

Treatments were applied as follows: All treatments were applied in 20 ml total spray volume per plant using a single, hand-held boom equipped with a solid-cone TG-3 tip at 35 psi. All treatments containing more than one chemical or formulation were applied as tank-mix combinations. Individual treatments were applied at the indicated rates. Each treatment consisted of 4 replications with each replication consisting of 1 plant. Evaluations were made by counting and weighing all suckers at about 6 weeks following initial treatment application. The results of these tests are shown below in Table 2. These results show excellent control of suckers using low rates of maleic hydrazide in combination with C18 fatty acids.

TABLE 2.

Percent control of tobacco suckers achieved using combinations of C18 fatty acids with maleic hydrazide.

| C18 Fatty Acid | Maleic Hydrazide (lb a.i./A) | |
|---|---|---|
| (quarts/acre) | 0 | 0.562 |
| 0 | 0 | 63.3 |
| 0.25 | NT | 63.0 |
| 0.50 | NT | 76.0 |
| 1.0 | 7.3 | 86.6 |

TABLE 2.-continued

Percent control of tobacco suckers achieved using combinations of C18 fatty acids with maleic hydrazide.

| C18 Fatty Acid | Maleic Hydrazide (lb a.i./A) | |
|---|---|---|
| (quarts/acre) | 0 | 0.562 |
| 2.0 | NT | 93.0 |

NT = not tested

It should be understood that the examples and embodiments described herein are for illustrative purposes only and that various modifications or changes in light thereof will be suggested to persons skilled in the art and are to be included within the spirit and purview of this application and the scope of the appended claims.

I claim:

1. An agricultural composition for controlling sucker growth in tobacco, said composition consisting essentially of a first component which is a monocarboxylic acid having about seven to about twenty-four carbon atoms, or a salt thereof, or a mixture of said acids or salts, and a second component which is a compound selected from the group consisting of flumetralin and maleic hydrazide; wherein said monocarboxylic acid or salt thereof can be represented by the following formula:

$$R_1Y_1Y_2COOR_2$$

wherein $R_1$=C6 to C23 saturated or unsaturated hydrocarbon, or an epoxide, or cyclopropane thereof;

$Y_1$=H, C1–C5 hydrocarbon, or hydroxy at any position along $R_1$;

$Y_2$=H, C1–C5 hydrocarbon, or hydroxyl at any position along $R_1$; and $R_2$=H, or salt; and wherein said first component is present in an amount that results in an application rate of greater than 0.25 quarts/acre when said composition is administered to control sucker growth in tobacco.

2. The composition, according to claim 1, wherein said first component comprises at least one monocarboxylic acid, or its salt, having from about seventeen to about nineteen carbons.

3. The composition, according to claim 2, wherein said first component comprises oleic acid or a salt thereof.

4. The composition, according to claim 3, wherein said first component is a mixture of oleic, linoleic, and linolenic acids or salts thereof.

5. The composition, according to claim 1, wherein said salt is selected from the group consisting of sodium, potassium, lithium, magnesium, and amine salts.

6. The composition, according to claim 1, wherein said first component comprises a salt of a fatty acid having about 9 carbons wherein said salt is selected from the group consisting of sodium, potassium, lithium, magnesium, and amine salts.

7. The composition, according to claim 1, wherein said second component comprises maleic hydrazide.

8. The composition, according to claim 1, wherein said first component comprises oleic acid or a salt thereof and said second component comprises maleic hydrazide.

* * * * *